US012746191B2

(12) United States Patent
Tachon et al.

(10) Patent No.: US 12,746,191 B2
(45) Date of Patent: Sep. 29, 2026

(54) STABILIZATION OF THIOPYRIDINONE COMPOUND AND YELLOWING REDUCTION OF COMPOSITION COMPRISING SAME

(71) Applicant: L'OREAL, Paris (FR)

(72) Inventors: Romain Tachon, Kawasaki (JP); Amelie Prevot-Gueguiniat, Aulnay-Sous-Bois (FR); Makoto Saito, Kawasaki (JP)

(73) Assignee: L'OREAL, Paris (FR)

( * ) Notice: Subject to any disclaimer, the term of this patent is extended or adjusted under 35 U.S.C. 154(b) by 314 days.

(21) Appl. No.: 18/267,333

(22) PCT Filed: Dec. 10, 2021

(86) PCT No.: PCT/JP2021/046653
§ 371 (c)(1),
(2) Date: Jun. 14, 2023

(87) PCT Pub. No.: WO2022/138471
PCT Pub. Date: Jun. 30, 2022

(65) Prior Publication Data

US 2024/0082132 A1 Mar. 14, 2024

(30) Foreign Application Priority Data

Dec. 22, 2020 (JP) ................................ 2020-212330
Jan. 18, 2021 (FR) ...................................... 2100459

(51) Int. Cl.
*A61K 8/49* (2006.01)
*A61Q 5/08* (2006.01)
*A61Q 19/02* (2006.01)

(52) U.S. Cl.
CPC .............. *A61K 8/4926* (2013.01); *A61Q 5/08* (2013.01); *A61Q 19/02* (2013.01)

(58) Field of Classification Search
CPC .............. A61K 8/4926; A61K 2800/52; A61K 8/4933; A61K 8/361; A61Q 5/08; A61Q 19/02
See application file for complete search history.

(56) References Cited

U.S. PATENT DOCUMENTS

2008/0193397 A1 8/2008 Kroll et al.
2019/0269581 A1* 9/2019 Tsubata .................... A61Q 1/12

FOREIGN PATENT DOCUMENTS

| | | | |
|---|---|---|---|
| CN | 108473432 | A | 8/2018 |
| CN | 109862940 | A | 6/2019 |
| JP | S53-005108 | A | 1/1978 |
| JP | S63-023846 | A | 2/1988 |
| JP | H05-124924 | A | 5/1993 |
| JP | 2015-048354 | A | 3/2015 |
| JP | 2019-500367 | A | 1/2019 |
| WO | 2006/122721 | A2 | 11/2006 |
| WO | 2012/080075 | A1 | 6/2012 |
| WO | 2017/102349 | A1 | 6/2017 |

OTHER PUBLICATIONS

Nurhan Dunford; "Canola Oil Properties"; Food Technology Fact Sheet FAPC-222; published Dec. 2018.*
Mason et al.; Biochemical and Biophysical Research Communications; 483 (2017), pp. 425-429. Published online Dec. 21, 2016.*
Office Action issued for the related Japanese patent application No. 2020-212330, mailed on Nov. 11, 2024, with machine English translation, 8 pages.
Wilma F. Bergfeld et al., Safety Assessment of Fatty Acids & Fatty Acid Salts as Used in Cosmetics, Status: Tentative Report for Public Comment, Jan. 4, 2019; 62 pages.
Marie Ollagnier et al., Formulating Towards Fairer Skin, Lubrizol, Jan. 1, 2011; 6 pages.
International Search Report for the corresponding patent application No. PCT/JP2021/046653 dated Mar. 14, 2022.
Office Action, dated Feb. 5, 2026, which was issued for the corresponding Chinese Patent Application No. 202180085788.9, 22 pages, with English translation.
Zhao Qinghua et al., "Double-Low Rapeseed New Varieties and Cultivation Techniques", Jindun Publishing House, Aug. 31, 2003, pp. 239-240.

* cited by examiner

*Primary Examiner* — Jeffrey T. Palenik
(74) *Attorney, Agent, or Firm* — LUCAS & MERCANTI, LLP

(57) ABSTRACT

The present invention relates to a composition comprising: (a) at least one thiopyridinone compound; and (b) at least one fatty acid comprising 18 or more carbon atoms, wherein the amount of the (b) fatty acid(s) comprising 18 or more carbon atoms in the composition is 10% by weight or more, preferably 12% by weight or more, and more preferably 14% by weight or more, relative to the total weight of the composition. The present invention can provide a composition including (a) thiopyridinone compound(s) with increased stability of the (a) thiopyridinone compound(s) over time, in particular even when the composition is maintained for a relatively long period of time under elevated temperature, and with reduced yellowing just after adding the thiopyridinone compound to the composition.

14 Claims, No Drawings

STABILIZATION OF THIOPYRIDINONE COMPOUND AND YELLOWING REDUCTION OF COMPOSITION COMPRISING SAME

CROSS REFERENCE TO RELATED APPLICATION

This Application is a 371 of PCT/JP2021/046653 filed on Dec. 10, 2021 which, in turn, claimed the priority of Japanese Patent Application No. 2020-212330 filed on Dec. 22, 2020 and French Patent Application No. 2100459 filed on Jan. 18, 2021, all of which are incorporated herein by reference.

TECHNICAL FIELD

The present invention relates to the stabilization of a thiopyridinone compound in a composition including the thiopyridinone compound and to the yellowing reduction of the composition.

BACKGROUND ART

At various periods of their life, some people see the appearance on their skin, and more in particular on the hands, of darker and/or more colored spots, which give the skin heterogeneity. These spots are in particular due to a high concentration of melanin in the keratinocytes located at the surface of the skin.

The use of harmless topical depigmenting substances with good efficacy is most particularly desired for the purpose of treating pigmentation spots.

For example, arbutin, niacinamide and kojic acid are known as skin depigmenting agents.

On the other hand, WO2017/102349 discloses a new depigmenting or whitening agent, i.e., a thiopyridinone compound. The thiopyridinone compound can show strong depigmenting or whitening effects by reducing the production of melanin.

DISCLOSURE OF INVENTION

However, it has been discovered that a thiopyridinone compound tends to be destabilized in a composition over time, in particular when the composition including the thiopyridinone compound is maintained for a relatively long period of time under elevated temperature, and that the composition including thiopyridinone compound tends to show intense yellow color just after the thiopyridinone compound is added to the composition.

Thus, an objective of the present invention is to provide a composition including thiopyridinone compound(s) with increased stability of the thiopyridinone compound(s) over time, in particular when the composition is maintained for a relatively long period of time under elevated temperature, and with reduced yellowing just after adding the thiopyridinone compound to the composition.

The above objective can be achieved by a composition comprising:

(a) at least one compound of formula (I)

(I)

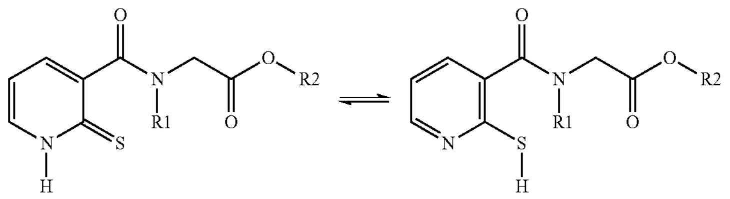

wherein

R1 denotes a radical chosen from:

a) a hydrogen atom; and b) a saturated linear $C_1$-$C_6$ alkyl group, and

R2 denotes a radical chosen from:

a) a hydrogen atom;

b) a saturated linear $C_1$-$C_{10}$ alkyl group;

c) a saturated branched $C_3$-$C_{10}$ alkyl group; and d) a $C_1$-$C_6$ phenylalkyl group such as benzyl, or a salt thereof, a solvate thereof, an optical isomer thereof, or a racemate thereof, and (b) at least one fatty acid comprising 18 or more carbon atoms, wherein the amount of the (b) fatty acid(s) comprising 18 or more carbon atoms in the composition is 10% by weight or more, preferably 12% by weight or more, and more preferably 14% by weight or more, relative to the total weight of the composition.

It is preferable that, in formula (I),

R1 denote a radical chosen from:

a) a hydrogen atom; and b) a saturated linear $C_1$-$C_4$ alkyl radical and preferably methyl, and R2 denote a radical chosen from:

a) a hydrogen atom;

b) a saturated linear $C_1$-$C_6$ alkyl group; and c) a saturated branched $C_3$-$C_6$ alkyl group.

It is more preferable that, in formula (I),

R1 denote a radical chosen from:

a) a hydrogen atom; and b) a methyl radical, and

R2 denote a radical chosen from:

a) a hydrogen atom;

b) a saturated linear $C_1$-$C_4$ alkyl group, preferably ethyl;

c) a saturated branched $C_3$-$C_6$ alkyl group, preferably isopropyl and isobutyl.

The (a) compound of formula (I) may be chosen from the following compounds:

| Structure | Compound No. | Chemical Name |
|---|---|---|
| 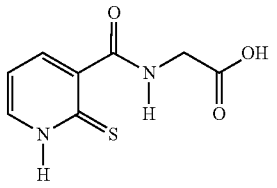 [SMILES: O=C(O)CNC(=O)c1ccc[nH]c1=S] | 1 | N-[(2-thioxo-1,2-dihydropyridin-3-yl) carbonyl]glycine |
| 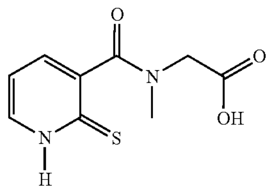 | 2 | N-methyl-N-[(2-thioxo-1,2-dihydropyridin-3-yl) carbonyl]glycine |

-continued

| Structure | Compound No. | Chemical Name |
|---|---|---|
| 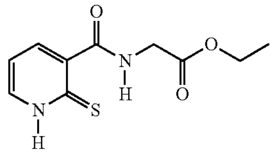 [SMILES: CCOC(=O)CNC(=O)c1ccc[nH]c1=S] | 3 | Ethyl N-[(2-thioxo-1,2-dihydropyridin-3-yl) carbonyl]glycinate |
| 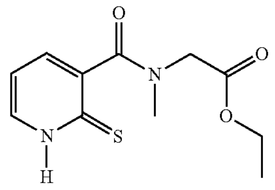 [SMILES: CCOC(=O)CN(C)C(=O)c1ccc[nH]c1=S] | 4 | Ethyl N-methyl-N-[(2-thioxo-1,2-dihydropyridin-3-yl) carbonyl]glycinate |

and salts thereof, solvates thereof, optical isomers thereof, and racemates thereof.

Preferably, the (a) compound of formula (I) may be chosen from the following compounds:

| Structure | Compound No. | Chemical Name |
|---|---|---|
| 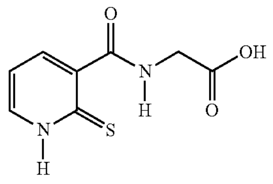 [SMILES: O=C(O)CNC(=O)c1ccc[nH]c1=S] | 1 | N-[(2-thioxo-1,2-dihydropyridin-3-yl) carbonyl]glycine |
| 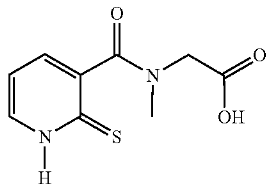 | 2 | N-methyl-N-[(2-thioxo-1,2-dihydropyridin-3-yl) carbonyl]glycine |

and salts thereof, solvates thereof, optical isomers thereof, and racemates thereof.

The amount of the (a) compound(s) of formula (I) in the composition according to the present invention may be from 0.01% to 20% by weight, preferably from 0.05% to 10% by weight, and more preferably from 0.1% to 5% by weight, relative to the total weight of the composition.

The (b) fatty acid comprising 18 or more carbon atoms may comprise 30 or less carbon atoms.

The (b) fatty acid comprising 18 or more carbon atoms may be selected from the group consisting of stearic acid, oleic acid, linoleic acid, arachidic acid, arachidonic acid, behenic acid, lignoceric acid, and nervonic acid.

The amount of the (b) fatty acid(s) comprising 18 or more carbon atoms in the composition according to the present invention may be from 10% to 35% by weight, preferably from 10% to 30% by weight, and more preferably from 10% to 25% by weight, relative to the total weight of the composition.

The composition according to the present invention may further comprise (c) at least one oil.

The composition according to the present invention may further comprise (d) water.

The composition according to the present invention may further comprise (e) at least one surfactant.

The composition according to the present invention may be for whitening a keratin substance, preferably skin.

The present invention also relates to a cosmetic process, preferably a whitening process, for a keratin substance, preferably skin, comprising the step of:

applying to the keratin substance the composition according to the present invention.

Another aspect of the present invention is a use of (b) at least one fatty acid comprising 18 or more carbon atoms in a composition comprising (a) at least one compound of formula (I)

(I)

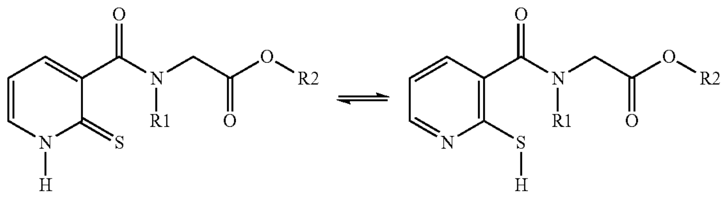

wherein

R1 denotes a radical chosen from:

a) a hydrogen atom; and b) a saturated linear $C_1$-$C_6$ alkyl group, and

R2 denotes a radical chosen from:

a) a hydrogen atom;

b) a saturated linear $C_1$-$C_{10}$ alkyl group;

c) a saturated branched $C_3$-$C_{10}$ alkyl group; and d) a $C_1$-$C_6$ phenylalkyl group such as benzyl, or a salt thereof, a solvate thereof, an optical isomer thereof, or a racemate thereof, wherein the amount of the (b) fatty acid(s) comprising 18 or more carbon atoms in the composition is 10% by weight or more, preferably 12% by weight or more, and more preferably 14% by weight or more, relative to the total weight of the composition, in order to stabilize the (a) compound(s) and reduce yellowing of the composition.

BEST MODE FOR CARRYING OUT THE INVENTION

After diligent research, the inventors have discovered that it is possible to provide a composition including a thiopyridinone compound or thiopyridinone compounds with increased stability of the thiopyridinone compound(s) over time, in particular even when the composition is maintained for a relatively long period of time under elevated temperature, and with reduced yellowing just after adding the thiopyridinone compound to the composition.

Thus, the composition according to the present invention comprises:

(a) at least one compound of formula (I)

(I)

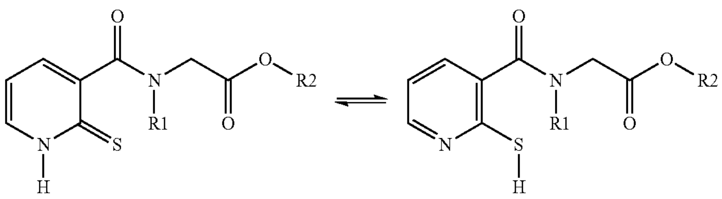

wherein

R1 denotes a radical chosen from:

a) a hydrogen atom; and b) a saturated linear $C_1$-$C_6$ alkyl group, and

R2 denotes a radical chosen from:

a) a hydrogen atom;

b) a saturated linear $C_1$-$C_{10}$ alkyl group;

c) a saturated branched $C_3$-$C_{10}$ alkyl group; and d) a $C_1$-$C_6$ phenylalkyl group such as benzyl, or a salt thereof, a solvate thereof, an optical isomer thereof, or a racemate thereof (hereafter, may be referred to as "(a) thiopyridinone compound"), and (b) at least one fatty acid comprising 18 or more carbon atoms, wherein the amount of the (b) fatty acid(s) comprising 18 or more carbon atoms in the composition is 10% by weight or more, preferably 12% by weight or more, and more preferably 14% by weight or more, relative to the total weight of the composition.

The composition according to the present invention can show increased stability of the (a) thiopyridinone compound therein.

In other words, the composition according to the present invention can increase the stability of the (a) thiopyridinone compound therein. The term "stability" of the (a) thiopyridinone compound can be determined by the change in the amount of the (a) thiopyridinone compound in the composition according to the present invention during a certain period of time. An increased "stability" means that the change in the amount of the (a) thiopyridinone compound over time is more limited.

The (a) thiopyridinone compound in a composition tends to decompose over time. Thus, the amount of the (a) thiopyridinone compound tends to reduce over time. Accordingly, an increased stability of the (a) thiopyridinone compound means that the reduction over time of the amount of the (a) thiopyridinone compound in a composition is restricted or smaller.

The composition according to the present invention can show increased stability of the (a) thiopyridinone compound therein, even when the composition is maintained for a relatively long period of time such as two months under elevated temperature such as 45° C.

The composition according to the present invention can also show increased stability of the (a) thiopyridinone compound therein, when the composition is maintained for a relatively long period of time such as two months under room temperature such as 25° C.

Therefore, the composition according to the present invention can be stored for a long period of time at both ambient and hot conditions, and in particular even under hot conditions.

In addition, the increased stability of the (a) thiopyridinone compound can provide improved or enhanced bioavailability of the (a) thiopyridinone compound which can function as a depigmenting or whitening agent. Therefore, the composition according to the present invention can provide enhanced or improved depigmenting or whitening effects.

The composition according to the present invention can also show reduced yellowing just after adding the thiopyridinone compound to the composition.

Without being bound by theory, the reduction in yellowing may be attributed to, at least, the formation of pearlescent or nacre structures by the (b) fatty acids comprising 18 or more carbon atoms, which could conceal or hide the yellow color of the composition according to the present invention.

The use of the (b) fatty acid comprising 18 or more carbon atoms in the composition according to the present invention, in an amount of 10% by weight or more relative to the total weight of the composition, can be sufficient to conceal or hide yellowing of the composition, just after adding the (a) thiopyridinone compound to the composition, under an acceptable level.

Hereafter, the composition, use and the like according to the present invention will be described in a detailed manner.

[Composition]

The composition according to the present invention comprises:

(a) at least one thiopyridinone compound; and (b) at least one fatty acid comprising 18 or more carbon atoms, wherein the amount of the (b) fatty acid(s) comprising 18 or more carbon atoms in the composition is 10% by weight or more, preferably 12% by weight or more, and more preferably 14% by weight or more, relative to the total weight of the composition.

The (a) thiopyridinone compound and (b) fatty acid comprising 18 or more carbon atoms, as well as the other features of the composition according to the present invention will be explained below.

(Thiopyridinone Compound)

The composition according to the present invention comprises (a) at least one thiopyridinone compound. Two or more (a) thiopyridinone compounds may be used in combination.

Thus, a single type of (a) thiopyridinone compound or a combination of different types of (a) thiopyridinone compounds may be used.

The (a) thiopyridinone compound may be an active ingredient or active compound in cosmetics or dermatological products. The term "active" ingredient or compound used herein means an ingredient or compound which has a cosmetic or dermatological active property, such as anti-oxidant, whitening, UV-filtering effects and anti-bacterial effects. The (a) thiopyridinone compound used in the present invention can function as a depigmenting, bleaching or whitening agent, and thus the composition according to the present invention may be used as a whitening product or as a cosmetic composition for a whitening keratin substance.

The (a) thiopyridinone compound may be used as an agent for depigmenting, bleaching or whitening the skin, body hairs, the eyelashes or head hair, and also the lips and/or the nails, and preferably the skin, in particular for eliminating pigmentation spots or senescence spots, and/or as an anti-tanning agent.

The (a) thiopyridinone compound is represented by the following formula (I)

(I)

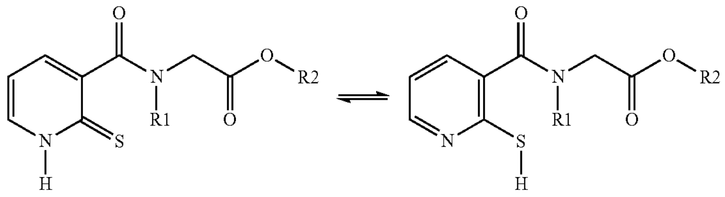

wherein

R1 denotes a radical chosen from:

a) a hydrogen atom; and b) a saturated linear $C_1$-$C_6$ alkyl group, and

R2 denotes a radical chosen from:

a) a hydrogen atom;

b) a saturated linear $C_1$-$C_{10}$ alkyl group;

c) a saturated branched $C_3$-$C_{10}$ alkyl group; and d) a $C_1$-$C_6$ phenylalkyl group such as benzyl, or a salt thereof, a solvate thereof, an optical isomer thereof, or a racemate thereof.

The salts of the compounds of formula (I) comprise the conventional non-toxic salts of said compounds, such as those formed from an acid or base.

As salts of the compounds of formula (I), mention may be made of:

the salts obtained by addition of the compound of formula (I) (when it comprises an acid group)

to a mineral base, such as sodium hydroxide, potassium hydroxide, calcium hydroxide, ammonium hydroxide, magnesium hydroxide, lithium hydroxide, and sodium, potassium or calcium carbonate or hydrogen carbonate for example;

or to an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made in particular of 2-amino-2-methylpropanol, ethanolamine, triethanolamine, 2-dimethylaminopropanol, 2-amino-2-(hydroxymethyl)-1,3-propanediol and 3-(dimethylamino)propylamine.

Mention may also be made of the salts of amino acids, for instance lysine, arginine, guanidine, glutamic acid and aspartic acid. Advantageously, the salts of the compounds of formula (I) (when it comprises an acid group) may be chosen from alkali metal or alkaline-earth metal salts such as sodium, potassium, calcium or magnesium salts; ammonium salts.

The acceptable solvates of the compounds described in the present invention comprise conventional solvates such as those formed during the preparation of said compounds owing to the presence of solvents. Mention may be made, by way of example, of the solvates due to the presence of water or of linear or branched alcohols, such as ethanol or isopropanol. The optical isomers are, in particular, enantiomers and diastereoisomers.

Preferentially, the linear or branched groups may be chosen from methyl, ethyl, propyl, isopropyl, butyl, isobutyl and tert-butyl, pentyl, hexyl, heptyl, octyl, nonyl and decyl.

More preferentially, the saturated linear or branched alkyl groups may be chosen from methyl, ethyl, propyl, isopropyl, butyl, isobutyl and tert-butyl, pentyl, hexyl, heptyl and octyl.

The compound a) is disclosed in the PubCHEM database (No. 47329290) http://pubchem.ncbi.nlm.nih.gov/compound/47329290?from=summary#section=Top entry: 2010-11-26.

The compound b) CAS>1240664-41-8 is described in the publication:

Synthesis of N-(2-mercaptopyridyl-3-formyl)-N-alkyl glycine and the corresponding disulfides Luo, Y. L.; Yang, Z. X.; Peng, S. X.

Div. Med. Chem., China Pharm. Univ., Nanjing, 210009, Peop. Rep. China

Yaoxue Xuebao (1990), 25(5), 374-8.

Preferably, the (a) thiopyridinone compounds of formula (I) have the following meanings:

R1 denotes a radical chosen from a) a hydrogen atom; and b) a saturated linear $C_1$-$C_4$ alkyl radical and preferably methyl, and R2 denotes a radical chosen from:

a) a hydrogen atom;

b) a saturated linear $C_1$-$C_6$ alkyl group; and c) a saturated branched $C_3$-$C_6$ alkyl group.

More preferably, the (a) thiopyridinone compounds of formula (I) have the following meanings:

R1 denotes a radical chosen from:

a) a hydrogen atom; and b) a methyl radical, and

R2 denotes a radical chosen from:

a) a hydrogen atom;

b) a saturated linear $C_1$-$C_4$ alkyl group, preferably ethyl;

c) a saturated branched $C_3$-$C_4$ alkyl group, preferably isopropyl and isobutyl.

The (a) thiopyridinone compound of formula (I) may be chosen from the following compounds:

| Structure | Compound No. | Chemical Name |
|---|---|---|
| 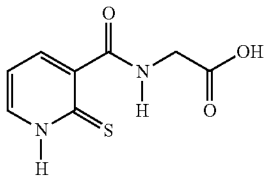 [SMILES: O=C(O)CNC(=O)c1ccc[nH]c1=S] | 1 | N-[(2-thioxo-1,2-dihydropyridin-3-yl)carbonyl]glycine |

-continued

| Structure | Compound No. | Chemical Name |
|---|---|---|
| 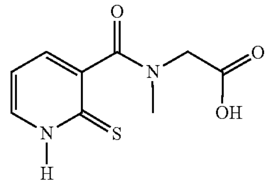 | 2 | N-methyl-N-[(2-thioxo-1,2-dihydropyridin-3-yl) carbonyl]glycine |
| 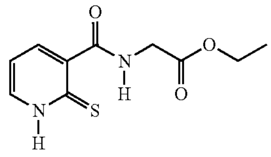 [SMILES: CCOC(=O)CNC(=O)c1ccc[nH]c1=S] | 3 | Ethyl N-[(2-thioxo-1,2-dihydropyridin-3-yl) carbonyl]glycinate |
| 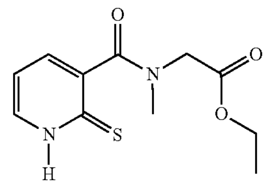 [SMILES: CCOC(=O)CN(C)C(=O)c1ccc[nH]c1=S] | 4 | Ethyl N-methyl-N-[(2-thioxo-1,2-dihydropyridin-3-yl) carbonyl]glycinate |

and salts thereof, solvates thereof, optical isomers thereof, and racemates thereof.

Preferably, the (a) thiopyridinone compound of formula (I) may be chosen from the following compounds:

| Structure | Compound No. | Chemical Name |
|---|---|---|
| 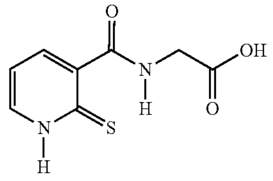 [SMILES: O=C(O)CNC(=O)c1ccc[nH]c1=S] | 1 | N-[(2-thioxo-1,2-dihydropyridin-3-yl) carbonyl]glycine |
| 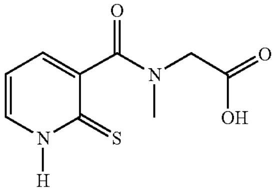 | 2 | N-methyl-N-[(2-thioxo-1,2-dihydropyridin-3-yl) carbonyl]glycine |

and salts thereof, solvates thereof, optical isomers thereof, and racemates thereof.

More preferably, the (a) thiopyridinone compound may be N-[(2-thioxo-1,2-dihydropyridin-3-yl)carbonyl]glycine.

The (a) thiopyridinone compound can be prepared in accordance with the process described in, for example, WO 2017/102349, which is herein incorporated by reference.

The amount of the (a) thiopyridinone compound(s) in the composition according to the present invention may be 0.01% by weight or more, preferably 0.05% by weight or more, and more preferably 0.1% by weight or more, relative to the total weight of the composition. It may be even more preferable that the amount of the (a) thiopyridinone compound(s) in the composition according to the present invention be 0.3% by weight or more, relative to the total weight of the composition.

On the other hand, the amount of the (a) thiopyridinone compound(s) in the composition according to the present invention may be 20% by weight or less, preferably 10% by weight or less, and more preferably 5% by weight or less, relative to the total weight of the composition. It may be even more preferable that the amount of the (a) thiopyridinone compound(s) in the composition according to the present invention be 3% by weight or less, relative to the total weight of the composition.

The amount of the (a) thiopyridinone compound(s) in the composition according to the present invention may range from 0.01% to 20% by weight, preferably from 0.05% to 10% by weight, more preferably from 0.1% to 5% by weight, relative to the total weight of the composition. It may be even more preferable that the amount of the (a) thiopyridinone compound(s) in the composition according to the present invention be from 0.3% to 3% by weight, relative to the total weight of the composition.

(Fatty Acid)

The composition according to the present invention comprises (b) at least one fatty acid comprising 18 or more carbon atoms (hereafter, may be referred to as "(b) fatty acid"). Two or more (b) fatty acids each of which comprises 18 or more carbon atoms may be used in combination. Thus, a single type of (b) fatty acid comprising 18 or more carbon atoms or a combination of different types of (b) fatty acids each of which comprises 18 or more carbon atoms may be used.

The term "fatty acid" here means a carboxylic acid with a long aliphatic carbon chain. It is preferable that the fatty acid be selected from saturated or unsaturated, linear or branched fatty acids. As the unsaturated, linear or branched fatty acids, mono-unsaturated, linear or branched fatty acids or polyunsaturated, linear or branched fatty acids may be used. As the unsaturated moiety of the unsaturated, linear or branched fatty acids, a carbon-carbon double bond or a carbon-carbon triple bond may be mentioned.

The (b) fatty acid may comprise 30 or less carbon atoms. It is preferable that the (b) fatty acid be selected from $C_{18}$-$C_{30}$ fatty acid, more preferably $C_{18}$-$C_{26}$ fatty acid, and even more preferably $C_{18}$-$C_{24}$ fatty acid.

As the (b) fatty acid, for example, a $C_{18}$-$C_{30}$ saturated, linear or branched fatty acid may be used. As $C_{18}$-$C_{30}$ saturated, linear or branched fatty acids, mention may be made of stearic acid (C18), nonadecanoic acid (C19), arachidic acid (C20), behenic acid (C22), and lignoceric acid (C24).

On the other hand, as the (b) fatty acid, for example, a $C_{18}$-$C_{30}$ unsaturated, linear or branched fatty acid may also be used. As the $C_{18}$-$C_{30}$ unsaturated, linear or branched fatty acids, mention may be made of oleic acid (C18), linoleic acid (C18), linolenic acid (C18), arachidonic acid (C20), and nervonic acid (C24).

The (b) fatty acid may be selected from the group consisting of stearic acid, oleic acid, linoleic acid, arachidic acid, arachidonic acid, behenic acid, lignoceric acid, and nervonic acid.

The (b) fatty acid may be in the form of a free acid or in the form of a salt thereof. As the salt of the fatty acid, mention may be made of an inorganic salt such as an alkali metal salt (a sodium salt, a potassium salt, or the like) and an alkaline earth metal salt (a magnesium salt, a calcium salt, or the like); and an organic salt such as an ammonium salt (a quaternary ammonium salt or the like) and an amine salt (a triethanolamine salt, a triethylamine salt, or the like). A single type of fatty acid salt or a combination of different types of fatty acid salts may be used. Further, a combination of one or more fatty acids in the form of a free acid and one or more fatty acids in the form of a salt may be used, in which one or more types of salts may also be used. It is preferable that at least a part (preferably at least 80%, and more preferably 90%), in particular all, of the fatty acids be in the form of a free acid.

The amount of the (b) fatty acid(s) comprising 18 or more carbon atoms in the composition according to the present invention is 10% by weight or more, preferably 12% by weight or more, and more preferably 14% by weight or more, relative to the total weight of the composition. It may be even more preferable that the amount of the (b) fatty acid(s) comprising 18 or more carbon atoms in the composition according to the present invention be 16% by weight or more, relative to the total weight of the composition.

On the other hand, the amount of the (b) fatty acid(s) comprising 18 or more carbon atoms in the composition according to the present invention may be 35% by weight or less, preferably 30% by weight or less, and more preferably 25% by weight or less, relative to the total weight of the composition. It may be even more preferable that the amount of the (b) fatty acid(s) comprising 18 or more carbon atoms in the composition according to the present invention be 20% by weight or less, relative to the total weight of the composition.

The amount of the (b) fatty acid(s) comprising 18 or more carbon atoms in the composition according to the present invention may range from 10% to 35% by weight, preferably from 12% to 30% by weight, more preferably from 14% to 25% by weight, relative to the total weight of the composition. It may be even more preferable that the amount of the (b) fatty acid(s) comprising 18 or more carbon atoms in the composition according to the present invention be from 16% to 20% by weight, relative to the total weight of the composition.

The weight ratio of the amount of (a) thiopyridinone compound(s) to the amount of (b) fatty acid(s) comprising 18 or more carbon atoms, in the composition according to the present invention, may be 10 or more, preferably 15 or more, and more preferably 30 or more.

(Oil)

The composition according to the present invention may comprise (c) at least one oil. If two or more (c) oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The (c) oil may be a non-polar oil such as a hydrocarbon oil, a silicone oil, or the like; a polar oil such as a plant or animal oil and an ester oil or an ether oil; or a mixture thereof.

The (c) oil may be selected from the group consisting of oils of plant or animal origin, synthetic oils, silicone oils, hydrocarbon oils, and fatty alcohols.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, etc.; cyclic organopolysiloxanes such as cyclohexasiloxane, octamethylcyclotetrasiloxane, decamethylcyclopentasiloxane, dodecamethylcyclohexasiloxane, etc.; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

If they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of a type such as dimethylsiloxane/methylalkylsiloxane, such as Silicone Volatile® FZ 3109 sold by the company Union Carbide, of the formula:

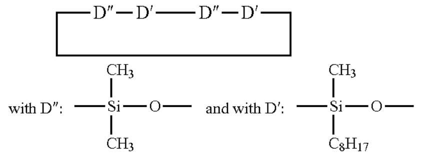

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5\times10^{-6}$ $m^2/s$ at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 $mm^2/s$; and
- the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

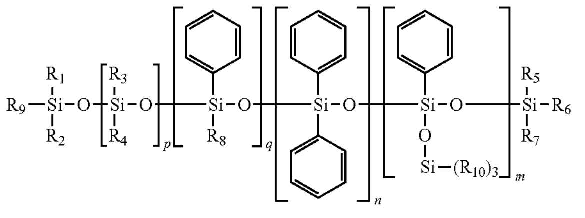

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:

- the Silbione® oils of the 70 641 series from Rhodia;
- the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, etc.; hydrogenated polyisobutene, isoeicosan, and decene/butene copolymer; and mixtures thereof.

The term "fatty" in the fatty alcohol means the inclusion of a relatively large number of carbon atoms. Thus, alcohols, which have 4 or more, preferably 6 or more, and more preferably 12 or more carbon atoms, are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It is also preferable that the (c) oil be chosen from oils with a molecular weight below 600 g/mol.

Preferably, the (c) oil has a low molecular weight such as below 600 g/mol, chosen among ester oils with a short hydrocarbon chain or chains ($C_1$-$C_{12}$) (e.g., isopropyl lauroyl sarcosinate, isopropyl myristate, isopropyl palmitate, isononyl isononanoate, and ethyl hexyl palmitate), silicone oils (e.g., volatile silicones such as cyclohexasiloxane), hydrocarbon oils (e.g., isododecane, isohexadecane, and squalane), branched and/or unsaturated fatty alcohol ($C_{12}$-$C_{30}$) type oils such as octyldodecanol and oleyl alcohol, and ether oils such as dicaprylylether.

The (c) oil may be chosen from volatile oils, non-volatile oils, and mixtures thereof.

The (c) oil may be chosen from polar and non-polar oils.

It is preferable that the (c) oil be selected from ester oils and silicone oils.

It is even more preferable that the (c) oil be chosen from non-volatile ester oils such as isopropyl myristate, and non-volatile silicone oils such as dimethicone.

The amount of the (c) oil(s) in the composition according to the present invention may be 0.1% by weight or more, preferably 0.5% by weight or more, and more preferably 1% by weight or more, relative to the total weight of the composition.

The amount of the (c) oil(s) in the composition according to the present invention may be 15% by weight or less, preferably 10% by weight or less, and more preferably 5% by weight or less, relative to the total weight of the composition.

The amount of the (c) oil(s) in the composition according to the present invention may be from 0.1% to 15% by weight, preferably from 0.5% to 10% by weight, and more preferably from 1% to 5% by weight, relative to the total weight of the composition.

(Water)

The composition according to the present invention may comprise (d) water.

The amount of the (d) water in the composition according to the present invention may be 50% by weight or more, preferably 60% by weight or more, and more preferably 70% by weight or more, relative to the total weight of the composition. It may be even more preferable that the amount of the (d) water in the composition according to the present invention be 75% by weight or more, relative to the total weight of the composition.

On the other hand, the amount of the (d) water in the composition according to the present invention may be 95% by weight or less, preferably 90% by weight or less, and more preferably 85% by weight or less, relative to the total weight of the composition. It may be even more preferable that the amount of the (d) water in the composition according to the present invention be 80% by weight or less, relative to the total weight of the composition.

The amount of (d) water in the composition according to the present invention may be from 50% to 95% by weight, preferably from 60% to 90% by weight, and more preferably from 70% to 85% by weight, relative to the total weight of the composition. It may be even more preferable that the amount of the (d) water in the composition according to the present invention be from 75% to 80% by weight, relative to the total weight of the composition.

(Surfactant)

The composition according to the present invention may comprise (e) at least one surfactant. If two or more surfactants are used, they may be the same or different.

Any surfactant may be used for the present invention. The (e) surfactant used in the present invention may be selected from the group consisting of anionic surfactants, amphoteric surfactants, cationic surfactants, and nonionic surfactants. Two or more surfactants may be used in combination. Thus, a single type of surfactant or a combination of different types of surfactants may be used.

The (e) surfactant may preferably be selected from the group consisting of nonionic surfactants.

(Anionic Surfactants)

According to the present invention, the type of anionic surfactant is not limited. It is preferable that the anionic surfactant be selected from the group consisting of ($C_6$-$C_{30}$) alkyl sulfates, ($C_6$-$C_{30}$)alkyl ether sulfates, ($C_6$-$C_{30}$)alkylamido ether sulfates, alkylaryl polyether sulfates, and monoglyceride sulfates; ($C_6$-$C_{30}$)alkylsulfonates, ($C_6$-$C_{30}$) alkylamide sulfonates, ($C_6$-$C_{30}$)alkylaryl sulfonates, α-olefin sulfonates, and paraffin sulfonates; ($C_6$-$C_{30}$)alkyl phosphates; ($C_6$-$C_{30}$)alkyl sulfosuccinates, ($C_6$-$C_{30}$)alkyl ether sulfosuccinates, and ($C_6$-$C_{30}$)alkylamide sulfosuccinates; ($C_6$-$C_{30}$)alkyl sulfoacetates; ($C_6$-$C_{24}$)acyl sarcosinates; ($C_6$-$C_{24}$)acyl glutamates; ($C_6$-$C_{30}$)alkylpolyglycoside carboxylic ethers; ($C_6$-$C_{30}$)alkylpolyglycoside sulfosuccinates; ($C_6$-$C_{30}$)alkyl sulfosuccinamates; ($C_6$-$C_{24}$)acyl isethionates; N-($C_6$-$C_{24}$)acyl taurates; $C_6$-$C_{30}$ fatty acid salts; coconut oil acid salts or hydrogenated coconut oil acid salts; ($C_8$-$C_{20}$)acyl lactylates; ($C_6$-$C_{30}$)alkyl-D-galactoside uronic acid salts; polyoxyalkylenated ($C_6$-$C_{30}$)alkyl ether carboxylic acid salts; polyoxyalkylenated ($C_6$-$C_{30}$)alkylaryl ether carboxylic acid salts; and polyoxyalkylenated ($C_6$-$C_{30}$)alkylamido ether carboxylic acid salts.

It is more preferable that the anionic surfactant be selected from salts of ($C_6$-$C_{30}$)alkyl sulfate or polyoxyalkylenated ($C_6$-$C_{30}$)alkyl ether carboxylic acid salts.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

(Amphoteric Surfactants)

According to the present invention, the type of amphoteric surfactant is not limited. The amphoteric or zwitterionic surfactants can be, for example (non-limiting list), amine derivatives such as aliphatic secondary or tertiary amine, and optionally quaternized amine derivatives, in which the aliphatic radical is a linear or branched chain comprising 8 to 22 carbon atoms and containing at least one water-solubilizing anionic group (for example, carboxylate, sulphonate, sulphate, phosphate, or phosphonate).

The amphoteric surfactant may preferably be selected from the group consisting of betaines and amidoaminecarboxylated derivatives.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$)alkylbetaines, ($C_8$-$C_{24}$)alkylamido($C_1$-$C_8$)alkylbetaines, sulphobetaines, and ($C_8$-$C_{24}$)alkylamido($C_1$-$C_8$)alkylsulphobetaines. In one embodiment, the amphoteric surfactants of betaine type are chosen from ($C_8$-$C_{24}$)alkylbetaines, ($C_8$-$C_{24}$)alkylamido($C_1$-$C_8$)alkylsulphobetaines, sulphobetaines, and phosphobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

$$R_1—CONHCH_2CH_2—N^+(R_2)(R_3)(CH_2COO^-)$$

in which:

$R_1$ denotes an alkyl radical of an acid $R_1$—COOH present in hydrolysed coconut oil, a heptyl, nonyl, or undecyl radical, $R_2$ denotes a beta-hydroxyethyl group, and $R_3$ denotes a carboxymethyl group; and $$R_1'—CONHCH_2CH_2—N(B)(C)$$

in which:

B represents —$CH_2CH_2OX'$,

C represents —$(CH_2)_z$-Y', with z=1 or 2,

X' denotes a —$CH_2CH_2$—COOH group, —$CH_2$—COOZ', —$CH_2CH_2$—COOH, —$CH_2CH_2$—COOZ', or a hydrogen atom, Y' denotes —COOH, —COOZ', —$CH_2$—CHOH—$SO_3Z'$, or a —$CH_2$—CHOH—$SO_3H$ radical, Z' represents an ion of an alkaline or alkaline earth metal such as sodium, an ammonium ion, or an ion issued from an organic amine, and $R_1'$ denotes an alkyl radical of an acid $R_1'$—COOH present in coconut oil or in hydrolysed linseed oil, an alkyl radical, such as a $C_7$, $C_9$, $C_{11}$, or $C_{13}$ alkyl radical, a $C_{17}$ alkyl radical and its iso form, or an unsaturated $C_{17}$ radical.

It is preferable that the amphoteric surfactant be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid, and Cocoamphodipropionic acid.

By way of example, mention may be made of the cocoamphodiacetate sold under the trade name Miranol® C2M concentrate by the company Rhodia Chimie.

(Cationic Surfactants)

According to the present invention, the type of cationic surfactant is not limited. The cationic surfactant may be selected from the group consisting of optionally polyoxyalkylenated, primary, secondary, or tertiary fatty amine salts, quaternary ammonium salts, and mixtures thereof.

Examples of quaternary ammonium salts that may be mentioned include, but are not limited to:

those of general formula (I) below:

(I)

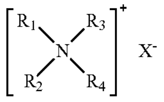

wherein $R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur, and halogens. The aliphatic radicals may be chosen, for example, from alkyl, alkoxy, $C_2$-$C_6$ polyoxyalkylene, alkylamide, $(C_{12}$-$C_{22})$alkylamido$(C_2$-$C_6)$alkyl, $(C_{12}$-$C_{22})$alkylacetate, and hydroxyalkyl radicals; and aromatic radicals such as aryl and alkylaryl; and $X^-$ is chosen from halides, phosphates, acetates, lactates, $(C_2$-$C_6)$ alkyl sulfates, and alkyl- or alkylaryl-sulfonates;

quaternary ammonium salts of imidazoline, for instance those of formula (II) below:

(II)

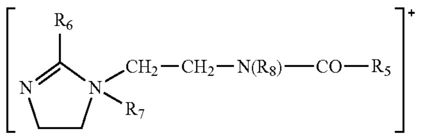

wherein:

$R_5$ is chosen from alkenyl and alkyl radicals comprising from 8 to 30 carbon atoms, for example fatty acid derivatives of tallow or of coconut;

$R_6$ is chosen from hydrogen, $C_1$-$C_4$ alkyl radicals, and alkenyl and alkyl radicals comprising from 8 to 30 carbon atoms;

$R_7$ is chosen from $C_1$-$C_4$ alkyl radicals;

$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl, and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG, and W75HPG by the company Witco;

diquaternary ammonium salts of formula (III):

(III)

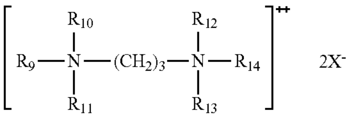

wherein:

$R_9$ is chosen from aliphatic radicals comprising from 16 to 30 carbon atoms;

$R_{10}$ is chosen from hydrogen or alkyl radicals comprising from 1 to 4 carbon atoms or the group $(R_{16a})(R_{17a})(R_{18a})N^+(CH_2)_3$;

$R_{11}$, $R_{12}$, $R_{13}$, $R_{14}$, $R_{16a}$, $R_{17a}$, and $R_{18a}$, which may be identical or different, are chosen from hydrogen and alkyl radicals comprising from 1 to 4 carbon atoms; and $X^-$ is chosen from halides, acetates, phosphates, nitrates, ethyl sulfates, and methyl sulfates.

An example of one such diquaternary ammonium salt is FINQUAT CT-P of FINETEX (Quaternium-89) or FINQUAT CT of FINETEX (Quaternium-75); and quaternary ammonium salts comprising at least one ester function, such as those of formula (IV) below:

wherein:

(IV)

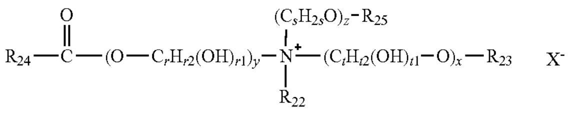

$R_{22}$ is chosen from $C_1$-$C_6$ alkyl radicals, and $C_1$-$C_6$ hydroxyalkyl and dihydroxyalkyl radicals;

$R_{23}$ is chosen from:

the radical below:

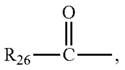

linear and branched, saturated and unsaturated $C_1$-$C_{22}$ hydrocarbon-based radicals $R_{27}$, and hydrogen, $R_{25}$ is chosen from:

the radical below:

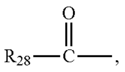

linear and branched, saturated and unsaturated $C_1$-$C_6$ hydrocarbon-based radicals $R_{29}$, and hydrogen, $R_{24}$, $R_{26}$, and $R_{28}$, which may be identical or different, are chosen from linear and branched, saturated and unsaturated, $C_7$-$C_{21}$, hydrocarbon-based radicals;

r, s, and t, which may be identical or different, are chosen from integers ranging from 2 to 6;

each of r1 and t1, which may be identical or different, is 0 or 1, and r2+r1=2r and t1+2t=2t;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is the hydrocarbon-based radical $R_{27}$, it may be long and comprise from 12 to 22 carbon atoms, or short and comprise from 1 to 3 carbon atoms. When $R_{25}$ is the hydrocarbon-based radical $R_{29}$, it may comprise, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s, and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium comprising an ester function, are other non-limiting examples of anions that may be used according to the present invention. In one embodiment, the anion $X^-$ is chosen from chloride and methyl sulfate.

In another embodiment, the ammonium salts of formula (IV) may be used, wherein:

$R_{22}$ is chosen from methyl and ethyl radicals, x and y are equal to 1;

z is equal to 0 or 1;

r, s, and t are equal to 2;

$R_{23}$ is chosen from:

the radical below:

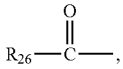, methyl, ethyl, and $C_{14}$-$C_{22}$ hydrocarbon-based radicals, and hydrogen;

$R_{25}$ is chosen from:

the radical below:

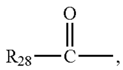, and hydrogen;

$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (IV) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of mono acyloxyethyl-hydroxyethyl-dimethyl-ammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine, or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the compositions according to the present invention include the ammonium salts comprising at least one ester function described in U.S. Pat. Nos. 4,874,554 and 4,137,180.

Among the quaternary ammonium salts mentioned above that may be used in the compositions according to the present invention include, but are not limited to, those corresponding to formula (I), for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium, and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the compositions of the present invention is chosen from quaternary ammonium salts, for example from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(Nonionic Surfactants)

The nonionic surfactants are compounds well known in and of themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N-($C_6$-$C_{24}$)alkylglucamine derivatives; amine oxides such as ($C_{10}$-

$C_{14}$)alkylamine oxides or N-($C_{10}$-$C_{14}$)acylaminopropylmorpholine oxides; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:

monooxyalkylenated or polyoxyalkylenated ($C_8$-$C_{24}$)alkylphenols, saturated or unsaturated, linear or branched, monooxyalkylenated or polyoxyalkylenated $C_8$-$C_{30}$ alcohols, saturated or unsaturated, linear or branched, monooxyalkylenated or polyoxyalkylenated $C_8$-$C_{30}$ amides, esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the nonionic surfactants do not comprise any oxypropylene units.

According to one of the embodiments of the present invention, the polyoxyalkylenated nonionic surfactants are chosen from polyoxyethylenated fatty alcohol (polyethylene glycol ether of fatty alcohol), polyoxyethylenated fatty ester (polyethylene glycol ester of fatty acid), and a mixture of polyoxyethylenated fatty alcohol and polyoxyethylenated fatty ester.

Examples of polyoxyethylenated fatty alcohol (or $C_8$-$C_{30}$ alcohols) that may be mentioned include the adducts of ethylene oxide with lauryl alcohol, especially those containing from 2 to 50 oxyethylene units and more particularly those containing from 2 to 20 oxyethylene units (Laureth-2 to Laureth-20, as the CTFA names); the adducts of ethylene oxide with behenyl alcohol, especially those containing from 2 to 50 oxyethylene units and more particularly those containing from 2 to 20 oxyethylene units (Beheneth-2 to Beheneth-20, as the CTFA names); the adducts of ethylene oxide with cetearyl alcohol (mixture of cetyl alcohol and stearyl alcohol), especially those containing from 2 to 30 oxyethylene units (Ceteareth-2 to Ceteareth-30, as the CTFA names); the adducts of ethylene oxide with cetyl alcohol, especially those containing from 2 to 30 oxyethylene units (Ceteth-2 to Ceteth-30, as the CTFA names); the adducts of ethylene oxide with stearyl alcohol, especially those containing from 2 to 50 oxyethylene units and more particularly those containing from 2 to 20 oxyethylene units (Steareth-2 to Steareth-20, as the CTFA names); the adducts of ethylene oxide with isostearyl alcohol, especially those containing from 2 to 50 oxyethylene units (Isosteareth-2 to Isosteareth-50, as the CTFA names); and mixtures thereof.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

According to one preferred embodiment of the present invention, the composition according to the present invention may comprise at least one polyoxyethylenated fatty alcohol.

According to a more preferred embodiment, the composition according to the present invention contains at least one fatty alcohol comprising from 2 to 9 ethyleneoxide units and at least one fatty alcohol comprising from 10 to 30 ethyleneoxide units.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

$$RO—[CH_2—CH(CH_2OH)—O]_m\text{-}H \quad \text{or}$$
$$RO—[CH(CH_2OH)—CH_2O]_m—H$$

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The monoglycerolated or polyglycerolated $C_8$-$C_{40}$ fatty esters may correspond to the following formula:

$$R'O—[CH_2—CH(CH_2OR''')—O]_m—R'' \quad \text{or}$$
$$R'O—[CH(CH_2OR''')—CH_2O]_m—R''$$

in which each of R', R" and R'" independently represents a hydrogen atom, or a linear or branched $C_8$-$C_{40}$ and preferably $C_8$-$C_{30}$ alkyl-CO— or alkenyl-CO-radical, with the proviso that at least one of R', R" and R'" is not a hydrogen atom, and m represents a number ranging from 1 to 30 and preferably from 1.5 to 10.

Preferably, the nonionic surfactant may be a nonionic surfactant with an HLB from 8 to 18. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

The amount of the (e) surfactant(s) in the composition according to the present invention may be 0.1% by weight or more, preferably 0.5% by weight or more, and more preferably 1% by weight or more, relative to the total weight of the composition.

The amount of the (e) surfactant(s) in the composition according to the present invention may be 10% by weight or less, preferably 5% by weight or less, and more preferably 3% by weight or less, relative to the total weight of the composition.

The amount of the (e) surfactant(s) in the composition according to the present invention may be from 0.1% to 10% by weight, preferably from 0.5% to 5% by weight, and more preferably from 1% to 3% by weight, relative to the total weight of the composition.

(Other Optional Additives)

The composition according to the present invention may also comprise any other optional additive(s) usually used in the field of cosmetics, chosen, for example, from anionic, cationic, amphoteric or nonionic polymers, solvents, thickening agents, dispersants, antioxidants, film-forming agents, preserving agents, fragrances, neutralizers, pH adjusting agents, antiseptics, UV-screening agents, cosmetic active agents other than ingredient (a), such as vitamins, moisturizers, emollients or collagen-protecting agents, and mixtures thereof.

It is a matter of routine operations for a person skilled in the art to adjust the nature and amount of the above optional additives which may be present in the composition in accordance with the present invention such that the desired cosmetic properties are not thereby affected.

As the solvents, mention may be made of one or several cosmetically acceptable organic solvents, which may be alcohols: in particular monovalent alcohols such as ethyl alcohol, isopropyl alcohol, benzyl alcohol, and phenylethyl alcohol; diols such as ethylene glycol, propylene glycol, and butylene glycol; other polyols such as glycerol, sugar, and sugar alcohols; and ethers such as ethylene glycol monomethyl, monoethyl, and monobutyl ethers, propylene glycol monomethyl, monoethyl, and monobutyl ether, and butylene glycol monomethyl, monoethyl, and monobutyl ethers.

The organic solvent(s) may be present in a concentration of from 0.01% to 30% by weight, preferably from 0.1% to 20% by weight, and more preferably from 1% to 15% by weight, relative to the total weight of the composition.

As the pH adjusting agent, at least one acidifying agent and/or at least one basifying agent (alkaline agent) may be used.

The acidifying agents can be, for example, mineral or organic acids, for instance hydrochloric acid, phosphoric acid, carboxylic acids, for instance tartaric acid, citric acid, and lactic acid, or sulphonic acids.

The basifying agent or alkaline agent can be, for example, any inorganic or organic basic agents which are commonly used in cosmetic products such as ammonia; alkanolamines such as mono-, di- and tri-ethanolamine, isopropanolamine; metal hydroxide such as alkaline metal hydroxide (e.g., sodium and potassium hydroxides); urea, guanidine and their derivatives; and diamines such as those described in the structure below:

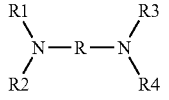

wherein

R denotes an alkylene such as propylene optionally substituted by a hydroxyl or a $C_1$-$C_4$ alkyl radical, and $R_1$, $R_2$, $R_3$, and $R_4$ independently denote a hydrogen atom, an alkyl radical, or a $C_1$-$C_4$ hydroxyalkyl radical, which may be exemplified by 1,3-propanediamine, and derivatives thereof. Alkaline metal hydroxide such as sodium hydroxide or potassium hydroxide may be preferable.

The acidifying agent and/or at least one basifying agent may be present in an amount ranging from less than 5% by weight, preferably from 3% by weight or less, and more preferably from 1% by weight or less, relative to the total weight of the composition.

[Preparation]

The composition according to the present invention can be prepared by mixing the above-described essential and optional ingredients in a conventional manner.

For example, the composition according to the present invention can be prepared by a process comprising the steps of mixing (a) at least one thiopyridinone compound; and (b) at least one fatty acid comprising 18 or more carbon atoms, in a composition wherein the amount of the (b) fatty acid(s) comprising 18 or more carbon atoms in the composition is 10% by weight or more, preferably 12% by weight or more, and more preferably 14% by weight or more, relative to the total weight of the composition.

It is possible to further mix any of the optional ingredients.

The mixing can be performed at any temperature such as room temperature (e.g., 20-25° C., preferably at 25° C.), preferably at a temperature of 30° C. or more, preferably 40° C. or more, and more preferably 50° C. or more. It is preferable to further mix with any of the above-described optional ingredients such as a pH adjusting agent.

The form of the composition according to the present invention is not particularly limited, and may take various forms such as a W/O emulsion, an O/W emulsion, a gel, a solution, or the like. It is preferable that the composition according to the present invention be in the form of an emulsion, preferably an O/W emulsion, and more preferably an O/W gel emulsion.

[Cosmetic Process]

The composition according to the present invention may be used as a cosmetic or dermatologic composition, preferably a cosmetic composition, and more preferably a cosmetic composition for a keratin substance. As the keratin substance, mention may be made of the skin, scalp, hair, mucosa such as lips, and nails.

The composition according to the present invention may be used as a depigmenting, bleaching or whitening product for a keratinous substance such as skin. In particular, the composition according to the present invention may be used as a whitening product.

The composition according to the present invention may preferably be intended for application onto a keratin substance such as the skin, scalp and/or the lips, preferably the skin.

Thus, the composition according to the present invention can be used for a cosmetic process for a keratin substance, preferably the skin. In one embodiment, the present invention relates to a cosmetic process, preferably a whitening process, for a keratin substance, preferably skin, comprising the step of applying onto the keratin substance the composition according to the present invention.

The composition according to the present invention can be used as a topical cosmetic composition in the form of a lotion, a milky lotion, a cream, a gel, a paste, a serum, foam, or spray.

[Use]

The present invention also relates to a use of (b) at least one fatty acid comprising 18 or more carbon atoms in a composition comprising (a) at least one compound of formula (I)

(I)

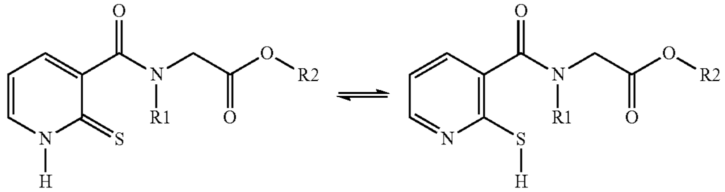

wherein

R1 denotes a radical chosen from:

a) a hydrogen atom; and b) a saturated linear $C_1$-$C_6$ alkyl group, and

R2 denotes a radical chosen from:

a) a hydrogen atom;

b) a saturated linear $C_1$-$C_{10}$ alkyl group;

c) a saturated branched $C_3$-$C_{10}$ alkyl group; and d) a $C_1$-$C_6$ phenylalkyl group such as benzyl, or a salt thereof, a solvate thereof, an optical isomer thereof, or a racemate thereof, wherein the amount of the (b) fatty acid(s) comprising 18 or more carbon atoms in the composition is 10% by weight or more, preferably 12% by weight or more, and more preferably 14% by weight or more, relative to the total weight of the composition, in order to stabilize the (a) compound(s) and reduce yellowing of the composition.

The term "stabilize" has the same meaning as enhancing stability.

The use according to the present invention can increase the stability of the (a) thiopyridinone compound in the composition comprising the same.

Therefore, the use according to the present invention can make it possible to store a composition comprising the (a) thiopyridinone compound for a long period of time at both ambient and hot conditions, and in particular even under hot conditions.

The use according to the present invention can also reduce yellowing of the composition comprising the (a) thiopyridinone compound, just after adding the (a) thiopyridinone compound to the composition.

Therefore, the use according to the present invention can enhance the aspect quality of the composition comprising the (a) thiopyridinone compound.

In other words, the use according to the present invention can make it possible to maintain the aspect of the composition comprising the (a) thiopyridinone compound for a long period of time at both ambient and hot conditions, and in particular even under hot conditions. Also, the use according to the present invention can make it possible to reduce or control yellowing of the composition, just after adding the (a) thiopyridinone compound to the composition.

The above explanations regarding the (a) thiopyridinone compound and the (b) fatty acid for the compositions according to the present invention can also apply to those used in the use according to the present invention.

The composition used in the use according to the composition may include any of the optional ingredients as explained above for the compositions according to the present invention.

EXAMPLES

The present invention will be described in a more detailed manner by way of examples. However, these examples should not be construed as limiting the scope of the present invention.

Examples 1-3 and Comparative Examples 1-4

[Preparation]

Each of the compositions according to Examples 1-3 and Comparative Examples 1-4 was prepared by mixing the ingredients shown in Table 1 in accordance with the following steps 1-8.

1. The ingredients for Phase A were mixed and heated to 80° C+/−5° C. to obtain a mixture of Phase A.
2. The ingredients for Phase B were mixed and heat to 80° C+/−5° C. to obtain a mixture of Phase B.
3. The mixture of Phase B was added to the mixture of Phase A, and the mixture thus obtained was homogenized with a homogenizer (TK robomix, PRIMIX) under 8,000 rpm at 80° C+/−5° C. for 10 minutes.
4. The ingredients for Phase C was further added to the above mixture obtained in Step 3, followed by homogenizing with the homogenizer under 8,000 rpm for 10 minutes.
5. The mixture obtained in Step 4 was cooled to 60° C+/−5° C. under slow agitation.
6. The ingredients for Phase D were mixed to obtain a mixture of Phase D.
7. The mixture of Phase D was added to the mixture obtained in Step 5 and mixed well under slow agitation.
8. The mixture obtained in Step 7 was cooled to room temperature under slow agitation.

The numerical values for the amounts of the ingredients are all based on "% by weight" as active raw materials.

TABLE 1

| Phase | Ingredients | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|---|
| A | Tetrasodium EDTA | 0.04 | 0.04 | 0.04 | 0.04 | 0.04 | 0.04 | 0.04 |
| A | Phenoxyethanol | 0.50 | 0.50 | 0.50 | 0.50 | 0.50 | 0.50 | 0.50 |
| A | Water | 57.09 | 56.24 | 62.24 | 65.24 | 68.26 | 56.26 | 56.26 |
| A | Glycerin | 1.00 | 1.00 | 1.00 | 1.00 | 1.00 | 1.00 | 1.00 |

TABLE 1-continued

| Phase | Ingredients | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|---|
| A | Hydroxyacetophenone | 0.40 | 0.40 | 0.40 | 0.40 | 0.40 | 0.40 | 0.40 |
| A | Potassium Cetyl Phosphate | 1.00 | 1.00 | 1.00 | 1.00 | 1.00 | 1.00 | 1.00 |
| B | Stearic Acid | 16.00 | 16.00 | 10.00 | 7.00 | 4.00 | — | — |
| B | Myristic Acid | — | — | — | — | — | — | 16.00 |
| B | Palmitic Acid | — | — | — | — | — | 16.00 | — |
| B | Cetyl Alcohol | 0.50 | 0.50 | 0.50 | 0.50 | 0.50 | 0.50 | 0.50 |
| B | Glyceryl Stearate (and) PEG-100 Stearate | 1.00 | 1.00 | 1.00 | 1.00 | 1.00 | 1.00 | 1.00 |
| B | Isopropyl Myristate | 1.00 | 1.00 | 1.00 | 1.00 | 1.00 | 1.00 | 1.00 |
| C | Dimethicone | 0.5 | 0.5 | 0.5 | 0.5 | 0.5 | 0.5 | 0.5 |
| C | Acrylates/C10-30 Alkyl Acrylate Crosspolymer | 0.12 | 0.12 | 0.12 | 0.12 | 0.12 | 0.12 | 0.12 |
| D | Water | 20.00 | 20.00 | 20.00 | 20.00 | 20.00 | 20.00 | 20.00 |
| D | Potassium Hydroxide | 0.35 | 0.70 | 0.70 | 0.70 | 0.68 | 0.68 | 0.68 |
| D | Compound No. 1 (N-[(2-thioxo-1,2-dihydropyridin-3-yl) carbonyl]glycine) | 0.50 | 1.00 | 1.00 | 1.00 | 1.00 | 1.00 | 1.00 |

[Evaluations]

(Thiopyridinone Quantification)

The amount of thiopyridinone in each of the compositions according to Examples 1-3 and Comparative Examples 1-4 was determined by an HPLC-UV assay at the following timing.

(1) Just after the preparation of the composition (T0)

(2) 2 months after the preparation, where the composition was maintained at room temperature (3) 2 month after the preparation, where the composition was maintained at 45° C.

The details of the HPLC-UV assay are as follows.

Apparatus/Reagents

| | |
|---|---|
| HPLC System | HPLC with UV detector |
| HPLC Column | C8 column 5 μm, 4 mm × 250 mm |
| Acetonitrile | HPLC grade |
| Monopotassium phosphate | Special grade |

HPLC Conditions

| | |
|---|---|
| UV detector | 220 nm |
| Column Temp. | 30° C. |
| Flow Rate | 1.0 mL/min |
| Injection Volume | 5 μL |
| Mobile Phase | Gradient mode<br>A: 0.01 mol/L monopotassium phosphate solution, |

-continued

| | |
|---|---|
| | pH = 3.0 with phosphoric acid<br>B: Acetonitrile |

The results are shown in Table 2.

(Color Evaluations)

(1) Instrumental Evaluation 10 g each of the compositions according to Examples 1-3 and Comparative Examples 1-4 just after the preparation thereof was filled in a 20 ml transparent glass vial. The b* value based on CIE1976 of the composition was measured by a spectrocolorimeter CM-700d (Konica Minolta) via the vial.

The results are shown in the line of "b*T0" in Table 2.

(2) Visual Evaluation 10 g each of the compositions according to Examples 1-3 and Comparative Examples 1-4 just after the preparation thereof was filled in a 20 ml transparent glass vial. The color of the composition was visually evaluated by 5 panelists in accordance with the following score criteria, and the scores were averaged.

0: white
1: very slightly yellow
2: slightly yellow
3: rather yellow
4: yellow
5: intense yellow The results are shown in the "Aspect" line in Table 2.

TABLE 2

| | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|
| Thiopyridinone (%) T0 | 0.5 | 1.08 | 1.07 | 1.07 | 1.05 | 1.03 | 1.06 |
| Thiopyridinone (%) RT, 2 M | 0.51<br>(+2.0%) | 1.00<br>(−7.4%) | 1.04<br>(−2.8%) | 1.03<br>(−3.7%) | 1.01<br>(−3.8%) | 0.94<br>(−8.7%) | 0.99<br>(−6.6%) |
| Thiopyridinone (%) 45° C., 2 M | 0.47<br>(−6.0%) | 0.97<br>(−10.2%) | 0.94<br>(−12.1%) | 0.93<br>(−13.1%) | 0.86<br>(−18.1%) | 0.90<br>(−12.6%) | 0.89<br>(−16.0%) |
| b* T0 | 9.38 | 15.66 | 17.62 | 19.03 | 19.65 | 21.15 | 21.02 |
| Aspect | 1 | 2 | 2.4 | 2.8 | 3.6 | 3.4 | 4 |

Thiopyridinone (%) T0: Just after the preparation of the composition

Thiopyridinone (%) RT, 2 M: 2 months after the preparation, where the composition was maintained at room temperature Thiopyridinone (%) 45° C., 2 M: 2 month after the preparation, where the composition was maintained at 45° C.

(Results)

The compositions according to Examples 1-3 each of which included a thiopyridinone compound and stearic acid (C18) in an amount of 10% by weight or more relative to the total weight of the composition were stable.

Specifically, the thiopyridinone compound in the compositions according to Examples 1-3 was more stable over time under both room temperature and elevated temperature than that in the compositions according to Comparative Examples 1-4.

Also, the color of the compositions according to Example 1-3 was only slightly yellow.

Comparative Example 1 shows that the amount (7% by weight) of stearic acid was insufficient to stabilize the thiopyridinone compound over time under elevated temperature and reduce yellowing to the level shown in Examples 1-3.

Comparative Example 2 also shows that the amount (4% by weight) of stearic acid was insufficient to stabilize the thiopyridinone compound over time under elevated temperature. Also, the composition according to Comparative Example 2 showed intense yellowing.

Comparative Example 3 shows that the use of myristic acid (C14) instead of stearic acid did not work to stabilize the thiopyridinone compound. Specifically, the thiopyridinone compound in the composition according to Comparative Example 3 was less stable over time under both room temperature and elevated temperature than that in the compositions according to Examples 1-3. Also, the composition according to Comparative Example 3 showed intense yellowing.

Comparative Example 4 shows that the use of palmitic acid (C16) instead of stearic acid did not work to stabilize the thiopyridinone compound. Specifically, the thiopyridinone compound in the composition according to Comparative Example 4 was less stable over time under elevated temperature than that in the compositions according to Examples 1-3. Also, the composition according to Comparative Example 4 showed intense yellowing.

The invention claimed is:

1. A composition, comprising:

(a) a compound being N-[(2-thioxo-1, 2-dihydropyridin-3-yl)carbonyl]glycine or a salt thereof, a solvate thereof, an optical isomer thereof, or a racemate thereof, and (b) at least one saturated fatty acid comprising 18 or more carbon atoms, wherein the (b) at least one saturated fatty acid is in a form of a free acid, and the amount of the (b) at least one saturated fatty acid comprising 18 or more carbon atoms in the composition is 10% to 16% by weight, relative to the total weight of the composition.

2. The composition according to claim 1, wherein the amount of the (a) compound being N-[(2-thioxo-1,2-dihydropyridin-3-yl)carbonyl]glycine, the salt thereof, the solvate thereof, the optical isomer thereof, or the racemate thereof in the composition is from 0.01% to 20% by weight, relative to the total weight of the composition.

3. The composition according to claim 1, wherein the (b) at least one saturated fatty acid comprising 18 or more carbon atoms comprises 30 or less carbon atoms.

4. The composition according to claim 1, wherein the (b) at least one saturated fatty acid comprising 18 or more carbon atoms is selected from the group consisting of stearic acid, arachidic acid, behenic acid, and lignoceric acid.

5. The composition according to claim 1, wherein the composition further comprises (c) at least one oil.

6. The composition according to claim 5, wherein the amount of the (c) at least one oil in the composition is 15% by weight or less, relative to the total weight of the composition.

7. The composition according to claim 1, wherein the composition further comprises (d) water.

8. The composition according to claim 7, wherein the amount of the (d) water in the composition is 50% by weight or more, relative to the total weight of the composition.

9. The composition according to claim 1, wherein the composition further comprises (e) at least one surfactant.

10. The composition according to claim 1, wherein the composition is for whitening a keratin substance.

11. The composition according to claim 1, wherein the amount of the (b) at least one saturated fatty acid comprising 18 or more carbon atoms in the composition is 12% by weight or more, relative to the total weight of the composition.

12. The composition according to claim 1, wherein the amount of the (b) at least one saturated fatty acid comprising 18 or more carbon atoms in the composition is 14% by weight or more, relative to the total weight of the composition.

13. A cosmetic process for a keratin substance, comprising:

applying to the keratin substance the composition according to claim 1.

14. A method for stabilizing (a) a compound being N-[(2-thioxo-1,2-dihydropyridin-3-yl)carbonyl]glycine, a salt thereof, a solvate thereof, an optical isomer thereof, or a racemate thereof and reducing yellowing of a composition containing the (a) compound being N-[(2-thioxo-1, 2-dihydropyridin-3-yl) carbonyl] glycine, the salt thereof, the solvate thereof, the optical isomer thereof, or the racemate thereof, comprising:

adding (b) at least one saturated fatty acid comprising 18 or more carbon atoms to the composition comprising the (a) compound being N-[(2-thioxo-1,2-dihydropyridin-3-yl)carbonyl]glycine, the salt thereof, the solvate thereof, the optical isomer thereof, or the racemate thereof wherein the (b) at least one saturated fatty acid is in a form of a free acid, and the amount of the (b) at least one saturated fatty acid comprising 18 or more carbon atoms in the composition is 10% 10 16% by weight, relative to the total weight of the composition.

* * * * *